United States Patent [19]

De Rigal et al.

[11] 4,396,025

[45] Aug. 2, 1983

[54] APPARATUS FOR MEASURING THE ELASTIC CHARACTERISTICS OF SKIN

[75] Inventors: Jean P. De Rigal, Claye-Souilly; Jean-Luc M. Leveque, Montfermeil, both of France

[73] Assignee: L'Oreal, Paris, France

[21] Appl. No.: 279,048

[22] Filed: Jun. 30, 1981

[30] Foreign Application Priority Data

Jul. 1, 1980 [FR] France ............................ 80 14659

[51] Int. Cl.³ .......................... A61B 5/00; A61B 5/10
[52] U.S. Cl. ..................................... 128/774; 128/782
[58] Field of Search .................. 128/56, 744, 774, 782, 128/790

[56] References Cited

U.S. PATENT DOCUMENTS 4,206,769 6/1980 Dikstein ............................. 128/774

FOREIGN PATENT DOCUMENTS 990162 6/1976 Canada .................................. 128/56
55-151242 11/1980 Japan .................................. 128/774
2016710 3/1979 United Kingdom .

OTHER PUBLICATIONS

Cook, T., et al., "Experimental Method for Determining the 2-Dimensional Mechanical Properties of Living Human Skin", Med. & Biol Eng. & Comput. 1977, 15, 381–390.

Gunner et al., "An Apparatus for Measuring the Recoil Characteristics of Human Skin in Vivo", Med. & Biol. Eng. & Comput. 1979, 17, 142–144.

Hutton et al., "An Apparatus for Measuring the Effects of Radiotherapy on the Elastic Properties of Skin in Vivo", Med. & Biol. Eng. 1975, vol. 13, No. 4, 584–585.

Daly et al. "Clinical Applications of Mechanical Impedance Measurements on Human Skin", presented at the 23rd annual Conf. on Eng. in Med. & Biol. Wash. 11/70.

Primary Examiner—Kyle L. Howell
Assistant Examiner—Christine A. Fukushima
Attorney, Agent, or Firm—N. Jerome Rudy

[57] ABSTRACT

The elastic properties of skin are measured by applying a torque to a disc placed in contact with a portion of the skin while holding a guard ring against skin around the region to define an annular skin sample to be stressed. Rotation of the disc is measured, and then the rotation is partially reversed and the torque-applying connection to the disc removed. The recovery rotation of the skin in the substantial absence of any applied torque is then measured.

12 Claims, 3 Drawing Figures

APPARATUS FOR MEASURING THE ELASTIC CHARACTERISTICS OF SKIN

DESCRIPTION

The present invention relates to the measurement of the elasticity of skin and, more particularly, the study in vivo of the elastic properties of the skin of a living subject.

For studying the properties of the human skin, it has already been known to apply to a portion of the skin a torque for a predetermined space of time and to examine the reactions of the said skin to the applied torsion stress. The results of such a measurement process are particularly useful for research concerning ageing of the skin, and for recognising the effects that certain cosmetic substances may have on the skin in the field of cosmetology.

Apparatuses of the type indicated above have already been proposed before. For example, in an article appearing in the "Biol. Med. Eng." Review, 6, pages 567 to 573, there has been described an apparatus comprising a disc to apply a torque on a portion of the skin to be studied; this disc is associated with a guard ring which is coaxial therewith and which is intended to be applied on the skin to delimit the portion of the skin subjected to examination around the disc. Driving means are connected to the disc to apply a moment around its axis whilst means of measurement determine the rotation of the disc. The behaviour of the skin is studied as, on the one hand, the response to the application of the moment by measuring the rotation of the disc and, on the other hand, its recovery behaviour when the applied moment is withdrawn (bringing about a reverse rotation of the disc under the effect of the return moment generated by the skin which is maintained in contact wtih the disc).

This known apparatus has several drawbacks. In the course of measurements of this kind, it is essential that any interference factors should be as small as possible. In other words, the elastic properties of the skin can only be measured with precision if, after the application of the moment, the disc is subjected solely to the return stress of the skin itself, to the exclusion of the stresses which may be introduced by the apparatus; this is all the more important since the intensity of the applied torsion stress is relatively weak in absolute values. In the above mentioned published article, this difficulty is not resolved satisfactorily because the driving means remains integral with the disc in rotation, even during the recovery phase. Another drawback derives from the fact that the apparatus is mounted in a fixed frame which necessitates the complete immobility of the portion of skin to be examined. For instance, if this portion is on the arm of the subject, it is necessary to keep this arm in a holding device during the whole measurement period which may last for several minutes; now such a constraint is tolerated with difficulty by a certain number of subjects, particularly by children and old people.

The object of the invention is to provide a measurement apparatus of the type indicated above wherein the drawbacks of the known apparatus are completely avoided.

One aspect of the present invention provides apparatus for measuring the elastic characteristics of skin by applying a torque thereto, said apparatus comprising: a rotatable disc for applying the torque during rotational movement along an angular travel; a guard ring which is coaxial with the disc and intended to be applied to the skin to delimit around the disc an annular skin sample to be subjected to the measurement; driving means connected to the disc to apply thereto a moment about its axis; and measurement means for determining the rotation of the disc; a one-way coupling effective to ensure the rotational connection between the disc and the driving means in a single direction of rotation; and means for achieving reversal of the direction of rotation of the driving means over a fraction of said angular travel after the moment has been applied to the disc.

In a preferred embodiment, the measurement means for determining the rotation of the disc comprise an angular displacement sensor whose moving element is fixed to the disc for rotation therewith; in this way, the apparatus constitutes a compact unit which may be held in the hand the thus manually applied to the skin to be examined, without the use of a fixed frame, the data provided by the angular displacement sensor which forms part of the apparatus being transmitted via a flexible connection to an appropriate read-out device such as, for example, a recording voltmeter; the complete integration of the measurement means into the apparatus according to the invention therefore makes it possible to keep the apparatus applied to the subject's skin without it being necessary to keep the subject's skin fixed in relation to a frame carrying all or part of the said measurement means, thereby obviating the need for attaching the subject partly to a fixed frame.

In an advantageous embodiment, the disc of the apparatus is carried by a shaft fixed to the moving element of the angular displacement sensor, the driving means are connected to a sleeve coaxial with the above mentioned shaft, the sleeve being connected with the shaft by means of a one-way coupling; the one way coupling comprises a key fixed on the shaft of the disc, the key cooperating with at least one drive dog which is integral with the sleeve; the driving means comprise an electric torque motor which is preferably reversible; the torque motor is mounted coaxially around the sleeve to which its rotor is fixed; stop means limit the travel of the rotor of the torque motor in the direction opposite to that along which the torque is applied to the skin; the stop means comprise at least one fixed stud relative to which the disc shaft and the sleeve rotate, the stud being arranged along the travel of at least one associated said drive dog when the sleeve is driven by the motor in the direction opposite to that during which the torque is applied to the skin to be examined; the above mentioned studs are given an angular displacement of approximately 90° in relation to the position of the above mentioned drive dogs at the commencement of driving of the disc when the torque is applied; the driving means are energised according to an asymmetrical cycle, the energy consumed in the period when the torque is applied being greater than that consumed in the period when the opposite rotation of the driving means takes place; the energy consumed during the period when the torque is applied is adjustable; the angular displacement sensor is an inductive transducer.

Another aspect of the invention provides an apparatus for measuring the elastic characteristics of skin in vivo, which applies a torque to a sample of the skin in a first direction; measures the torsional strain of the skin in response to the applied torque; reduces the torsional strain by a fraction thereof; and measures the recovery of the skin sample in the absence of any applied torque, wherein the torque is applied by a rotatable member in contact with the skin and driven by driving means releasably connected thereto, and the connection between the rotatable torque applying member and the driving means is released when the torsional strain is reduced thereby leaving the skin free to recover substantially without any torsional stress influence on the rotatable member whose reverse rotation is then measured.

It follows from these characteristics that the interference factors, deriving in particular from the effect of the driving means after the torque has been applied, are suppressed since these driving means become uncoupled from the disc when the rotation measured is that effected under the effect of the recovery torque generated by the skin. The means for ensuring the reversal of the direction of rotation of the driving means may be easily obtained by reversing the electric supply of a reversible torque motor.

In order that the present invention may more readily be understood there will now be described an embodiment represented, by way of a purely illustrative and non-restrictive example, in the attached drawings, in which.

Figure 1:
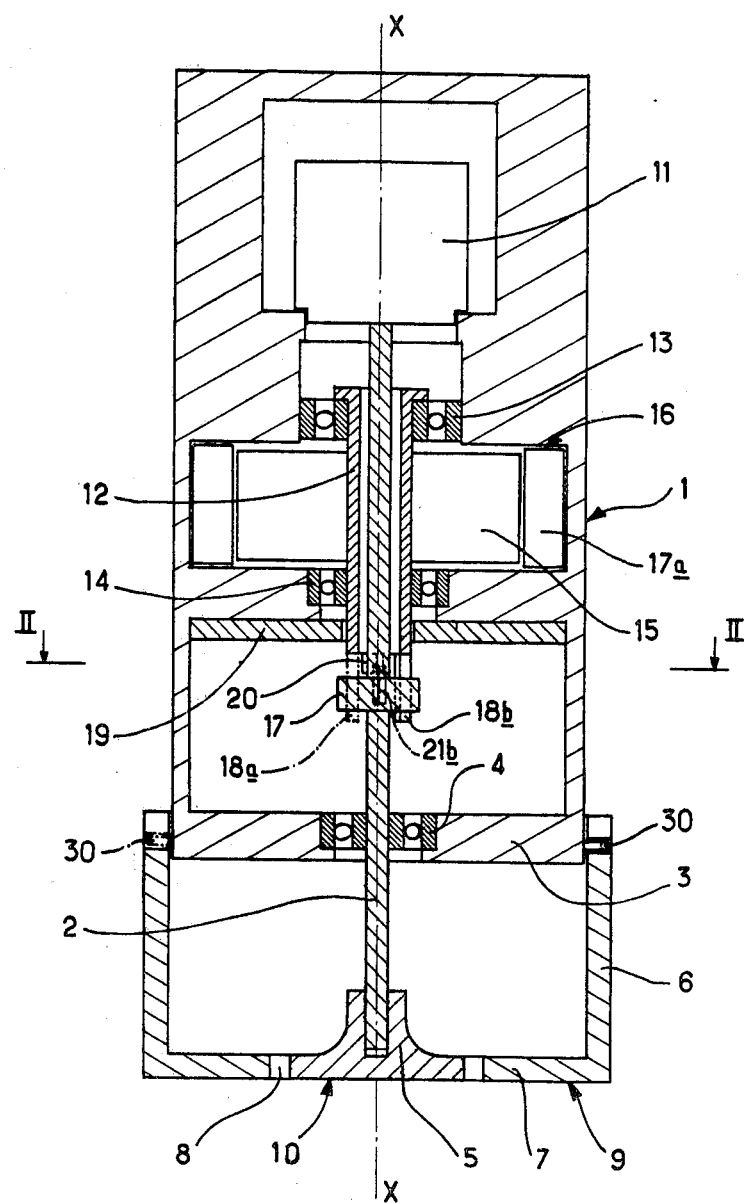
FIG. 1 shows a measurement apparatus according to the invention, as a schematic axial cross section taken along I—I of FIG. 2.

Referring to the drawings it will be seen that the measurement apparatus according to the invention comprises a generally cylindrical casing 1 whose dimensions are such that it may easily be held in the hand. A shaft 2, having its axis of rotation X—X disposed along the axis of this casing, passes through an end partition 3 of the casing where it is guided by a ball bearing 4. The free end of this shaft carries a disc 5 coaxial with axis X—X and intended, during the measurement, to be placed into contact with the portion of the skin to be examined. A skirt 6, fixed by one of its end edges to casing 1 by means of a bayonet fixing using two studs 30 of the casing, carries at its opposite end a guard ring 7 whose inner edge is spaced from the circumference of disc 5 by an annular gap 8. The outer face 9 of the guard ring 7 is situated in the same plane as the outer face 10 of disc 5. This fixing arrangement allows the guard ring 7 to be changed easily in dependence on the skin types to be studied.

The end of the shaft 2 away from the disc 5 is integral with the moving element of an angular displacement sensor 11 whose stator is rigidly mounted in casing 1. Sensor 11 can thus supply an electric signal representing the magnitude of the rotation imparted to disc 5, and may be of any conventional type. In the embodiment described, the sensor 11 is an inductive transducer sold under the designation "CIMATHI CR 90".

Figure 2:
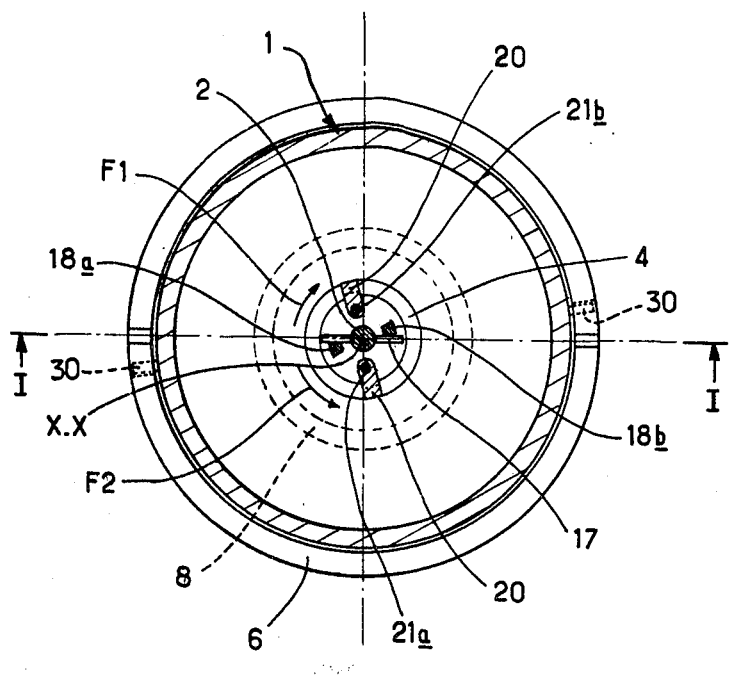
FIG. 2 is a cross section along line II—II of FIG. 1.

Within the casing 1, shaft 2 passes through a sleeve 12 rotatably mounted in this casing by means of ball bearings 13 and 14. This sleeve is secured for conjoint rotation with rotor 15 of a torque motor 16 whose stator 17a is rigidly mounted in the casing 1. The sleeve 12 is coaxial with axis X—X of the shaft 2. At the level of the free end (i.e. the lower end) of the sleeve 12, the shaft 2 is traversed by a key 17 constituted by a strip extending from one side to another of this shaft. This key 17 cooperates with axial drive dogs 18a, 18b extending the sleeve 12 at this end and extends radially beyond these axial drive dogs. The drive dogs are diametrically opposed to each other as is clearly seen in FIG. 2.

The compartment of the casing 1 in which the torque motor 16 is housed, is separated from the bottom part of the casing by a transverse partition 19 carrying the support 20 of stop studs 21a, 21b in diametrically opposed positions in relation to axis X—X. The studs are spaced from axis X—X at the same radial distance as the axial drive dogs 18a, 18b. If desired, only one such stop stud 21b and, optionally, only one drive dog 18b may be provided.

Figure 3:
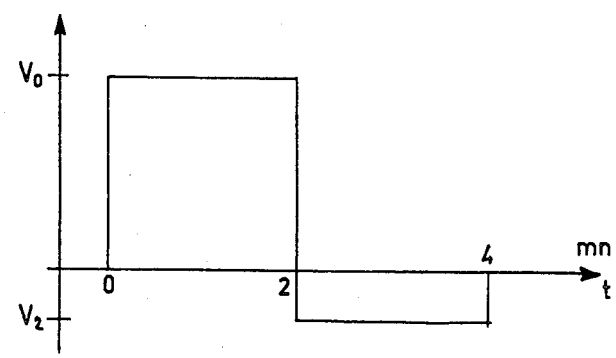
FIG. 3 is a graph showing the variation, with respect to time, of the supply voltage of the torque motor of the apparatus of FIG. 1 during one measurement cycle.

The functioning of the apparatus described above is as follows. When the apparatus is placed in its working position on a skin region to be examined, the guard ring 7 delimits around the disc 5 an annular skin sample, corresponding to the gap 8, to which a torque is to be applied. To achieve this, the operator activates the torque motor 16 with an electric voltage (in volts) whose variation with respect to time (in minutes) is represented in FIG. 3. The voltage applied may be chosen at a value appropriate for the measurement operation but it remains constant in the course of one measurement operation. The energisation by the positive voltage plateau produces the induced rotation of the sleeve 12 so that the axial drive dogs 18a and 18b apply a moment (in the direction of arrow F1) to the key 17 which forms part of the shaft 2. Thus there follows rotation of the disc 5 and the application of torque to the annular skin sample.

After this torque application has lasted for a predetermined time, two minutes for instance, the voltage applied to the torque motor 16 is suddenly reversed so that the sleeve 12 is driven in the reverse direction, the axial drive dogs 18a, 18b being suddenly disengaged from the key 17 and striking the stop studs 21a, 21b, the motion then taking place in the direction of arrow F2. The application of this reverse voltage may also be of two minutes duration. It is clear that the level of the reverse voltage may be low because it is only used to bring drive dogs 18a, 18b against the stop studs 21a, 21b and this second voltage plateau may be of short duration. The comparison of the areas enclosed between, on the one hand, the positive going part of the graph and, on the other hand, the negative going part of the graph, and the abscissa in each case, shows that more energy is used in the first part of the cycle than in the second.

Once the applied torque on the skin has been thus removed, the skin reaction is measured; that is to say, the rotation of disc 5 under the effect of the recovery torque generated by the skin is measured. During this period of measurement, the torque motor 16 has no effect on the measurement because the assembly of key 17 and of axial drive dogs 18a, 18b forms a one-way coupling ensuring the connection with the disc 5 only in the one direction applicable to the first phase of the measurement operation. The recovery torque exerted by the skin is therefore then measured by the angular displacement sensor 11 without any interference effect disturbing this measurement.

During the whole working cycle of this apparatus, the operator can easily hold the apparatus on the skin, even if the skin portion is located on a limb of the subject, because the apparatus can be held in the hand and the operator can thus easily follow any movements of the subject.

In the embodiment described, the reverse travel of the sleeve 12 and of torque motor 16 is limited by the mechanical stop studs 21a, 21b. In a variant of this embodiment, the reverse travel of these driving means could be limited by appropriate control of the voltage applied to the torque motor.

It shall be duly understood that the embodiment described above is in no way restrictive and may give rise to any desirable modifications without thereby departing from the scope of the invention as defined by the following claims.

We claim:

1. In apparatus for measuring the elastic characteristics of skin by applying a torque thereto, said apparatus comprising:
   (a) a disc rotatable about an axis along an angular travel for applying the torque;
   (b) a guard ring coaxial with the disc, to be applied to the skin to delimit around the disc an annular skin sample to be subjected to the measurement;
   (c) driving means connected to the disc to apply thereto a moment around its axis; and
   (d) measurement means for determining the rotation of the disc;
the improvement comprising:
   (e) one-way coupling means ensuring rotational connection between disc and the driving means in a single direction of rotation; and
   (f) means effective to achieve reversal of the direction of rotation of the driving means over a fraction of said angular travel after said moment has been applied to the disc.

2. Apparatus according to claim 1, wherein said measurement means comprise an angular displacement sensor having a stator and a moving element, and means fixing the moving element to the disc for rotation therewith.

3. Apparatus according to claim 2, wherein said means fixing the moving element to the disc means comprises a shaft fixed to the moving element of the angular displacement sensor and carrying the disc, and wherein said driving means include a sleeve coaxial with said shaft and connected thereto by way of said one-way coupling means.

4. Apparatus according to claim 3, wherein said one-way coupling means comprise a key fixed to said shaft, and drive dog means integral with said sleeve and cooperating with the key.

5. Apparatus according to any one of claims 1 to 4, wherein the apparatus constitutes a compact unit dimensioned and configured to be held in the human hand and thus manually applied against the skin to be examined.

6. Apparatus according to any one of claims 1 to 4, including means energising the driving means according to an asymmetric cycle in which the energy consumed during the torque application phase is greater than that consumed in the measurement phase when the reverse rotation of the driving means takes place after removal of the applied torque.

7. Apparatus according to any one of claims 1 to 4, wherein the measurement means comprise an inductive angular displacement transducer.

8. Apparatus according to any one of claims 1 to 4, wherein the driving means comprises an electric torque motor.

9. Apparatus according to claim 8, wherein the torque motor is mounted coaxially around the sleeve and has a rotor fixed thereto.

10. Apparatus according to claim 8, wherein the means for achieving reversal of the direction of rotation of the driving means over a fraction of said angular travel include stop means for limiting the travel of the rotor of the motor in the direction opposite to that in which the torque is applied to the skin.

11. Apparatus according to claim 10, wherein the stop means comprise at least one stud relative to which the shaft and the sleeve move, said at least one stud being positioned to interrupt the travel of an associated said drive dog when the sleeve is driven by the motor in the direction opposite to that during which the torque is applied to the skin sample to be examined.

12. Apparatus according to claim 11, wherein said at least one stud has an approximate angular displacement of 90° in relation to the position of the said associated drive dog at the start of the driving of the disc when the torque is applied.

* * * * *